United States Patent
Opore et al.

(10) Patent No.: US 8,050,666 B2
(45) Date of Patent: Nov. 1, 2011

(54) APPOINTMENT APPLICATION FOR USE IN ELECTRONIC EQUIPMENT

(75) Inventors: Francis Opore, Raleigh, NC (US); Yadav Parveen, Durham, NC (US)

(73) Assignee: Sony Ericsson Mobile Communications AB, Lund (SE)

( * ) Notice: Subject to any disclaimer, the term of this patent is extended or adjusted under 35 U.S.C. 154(b) by 803 days.

(21) Appl. No.: 12/029,674

(22) Filed: Feb. 12, 2008

(65) Prior Publication Data

US 2009/0203369 A1 Aug. 13, 2009

(51) Int. Cl.
*H04M 1/00* (2006.01)
(52) U.S. Cl. .............. 455/418; 455/575.1; 379/210.01
(58) Field of Classification Search .............. 455/575.1, 455/418; 379/210.01; 705/3
See application file for complete search history.

(56) References Cited

U.S. PATENT DOCUMENTS

| | | | | |
|---|---|---|---|---|
| 4,388,489 A * | 6/1983 | Wigan et al. | .................. | 178/3 |
| 4,783,800 A * | 11/1988 | Levine | .................. | 379/88.09 |
| 5,933,477 A * | 8/1999 | Wu | .................. | 379/88.26 |
| 5,933,778 A * | 8/1999 | Buhrmann et al. | .......... | 455/461 |
| 6,047,259 A * | 4/2000 | Campbell et al. | .......... | 705/3 |
| 6,584,490 B1 * | 6/2003 | Schuster et al. | .......... | 709/200 |
| 2002/0152107 A1 * | 10/2002 | Mifune et al. | .......... | 705/9 |
| 2003/0046304 A1 * | 3/2003 | Peskin et al. | .......... | 707/104.1 |
| 2003/0063732 A1 * | 4/2003 | Mcknight | .......... | 379/210.01 |
| 2004/0176973 A1 * | 9/2004 | Lapeze et al. | .......... | 705/1 |
| 2004/0220830 A1 * | 11/2004 | Moreton et al. | .......... | 705/2 |
| 2004/0223598 A1 * | 11/2004 | Spiridellis | .......... | 379/201.01 |
| 2005/0032527 A1 * | 2/2005 | Sheha et al. | .......... | 455/456.1 |
| 2005/0043010 A1 * | 2/2005 | Rosansky | .......... | 455/405 |
| 2005/0059384 A1 * | 3/2005 | Kuusinen et al. | .......... | 455/414.1 |
| 2005/0130631 A1 * | 6/2005 | Maguire et al. | .......... | 455/414.1 |
| 2006/0126818 A1 * | 6/2006 | Berger et al. | .......... | 379/265.09 |
| 2006/0136267 A1 * | 6/2006 | Brackett et al. | .......... | 705/3 |
| 2006/0142057 A1 * | 6/2006 | Schuler et al. | .......... | 455/556.1 |
| 2006/0147005 A1 * | 7/2006 | Taub | .......... | 379/114.2 |
| 2006/0178175 A1 * | 8/2006 | Miller | .......... | 455/575.1 |
| 2009/0070178 A1 * | 3/2009 | Gilbert | .......... | 705/8 |
| 2009/0138283 A1 * | 5/2009 | Brown | .......... | 705/3 |
| 2009/0203369 A1 * | 8/2009 | Opore et al. | .......... | 455/418 |

* cited by examiner

*Primary Examiner* — Charles Shedrick
(74) *Attorney, Agent, or Firm* — Renner, Otto, Boisselle & Sklar, LLP

(57) ABSTRACT

A method, device and computer program for coordinating a communication session between an individual and a user of a portable communication device. A portable communication device is provided having an appointment application program stored in memory. The appointment application program includes a queue indicative of a plurality of contacts that are required to contact an associated user of the portable communication device during a predetermined period from an authorized contact number. When the user of the portable communication device 10 receives a telephone call, the call is processed to determine if the telephone call is from one of the authorized contact numbers associated with one of the contacts from queue.

16 Claims, 3 Drawing Sheets

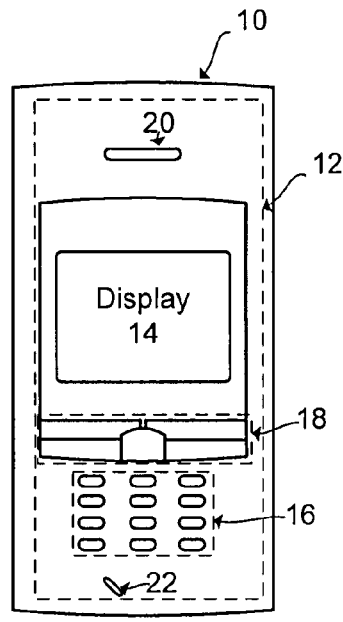
Figure 1
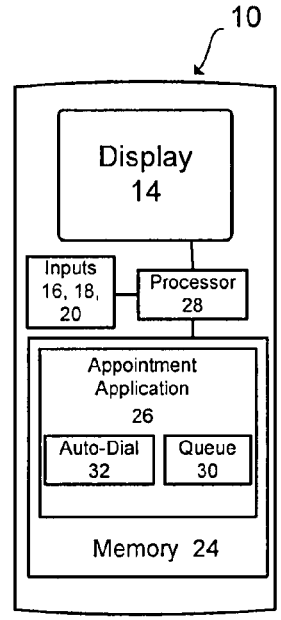
Figure 2
| QUEUE | Name | Telephone #1 | Telephone #2 | Telephone #3 | Freq. | Met Req. | RCU |
|---|---|---|---|---|---|---|---|
| 1 | Jane Doe | 440 1XX-5678 | | | Daily | Y | N |
| 2 | Alan | 3XX 987-1234 | 21X X21-1113 | | Daily | Y | N |
| 3 | Zack | 908 X1X-9X12 | | | Weekly | N | Y |
| 4 | Mo Rice | 525 X16-3X27 | 6X7 11X-1X11 | 64X 1X1-8XX8 | Monthly | N | N |
| * | * | * | * | * | * | * | * |
| * | * | * | * | * | * | * | * |
| * | * | * | * | * | * | * | * |
| N | Paige | 123 987-6543 | X67 XX0-9121 | | Monthly | Y | N |
Figure 3

APPOINTMENT APPLICATION FOR USE IN ELECTRONIC EQUIPMENT

TECHNICAL FIELD OF THE INVENTION

The present invention relates generally to an appointment application for use in electronic equipment and, more particularly, to electronic equipment and a method for managing telephone calls used in connection with monitoring of contacts.

DESCRIPTION OF THE RELATED ART

Effective medical treatment often times requires frequent monitoring of patients by their doctor or clinician. This frequent monitoring can significantly reduce the rate of complications and medical deterioration and can improve the return to, and maintenance of, mental and physical health of the patient. As a result, such patients generally experience fewer hospitalizations, improved level of health and a reduction in the cost of care provided to them.

Delivering such outpatient care is difficult to accomplish due to a variety of reasons. Long-term hospitalization is generally not an option because it confines a patient to a hospital. Frequent outpatient clinic visits present numerous logistical obstacles to the patient, which also makes it impractical. In addition, the costs associated with frequent outpatient care also are also prohibitive.

These problems are further aggravated when an individual, usually a professional (e.g., a doctor, psychiatrist, psychologist, lawyer, etc.), is required to be at a certain location to receive telephone calls from other individuals, patients and/or contacts over an extended period of time. Currently, there is no ability for the individual to leave the prescribed location and/or telephone, without taking additional call logs and/or other contact lists to ensure that all of the individuals, patients and/or contacts that were required to and/or supposed to call the individual actually, in fact, made their required call and actually spoke with the individual.

Given the above problems, it is desirable to have a system and method that enables periodic (e.g., daily, weekly, monthly, etc.) monitoring of individuals, patients and/or contacts without the need for specialized equipment and/or an individual to maintain contact logs and/or lists or remain at a fixed location.

SUMMARY

The present invention relates generally to an appointment application for use in electronic equipment and, more particularly, to electronic equipment and a method for managing telephone calls used in connection with contact monitoring.

One aspect of the invention relates to a method for coordinating a communication session between an individual and a user of a portable communication device, the method including: providing a portable communication device having a program stored in memory, wherein the program includes a queue indicative of a plurality of contacts that are required to contact an associated user of the portable communication device during a predetermined period from an authorized contact number; receiving a telephone call; processing the telephone call to determine if the telephone call is from one of the authorized contact numbers associated with one of the contacts from queue.

Another aspect of the invention relates to the portable communication device being a mobile telephone.

Another aspect of the invention relates to the authorized contact number being a telephone number.

Another aspect of the invention relates to if the user of the portable communication device is unavailable when the telephone call is received, a prerecorded message is rendered to the calling contact.

Another aspect of the invention relates to updating the queue to indicate receipt of the telephone call from the contact and the contact remains in the queue.

Another aspect of the invention relates to if the user of the portable communication device is available when the contact calls, the contact and the associated user converse as desired.

Another aspect of the invention relates to including updating the queue to indicate receipt of the telephone call from one of the contacts listed in the queue.

Another aspect of the invention relates to queue being updated by deleting the contact that initiated the telephone call from the queue.

Another aspect of the invention relates to when the telephone call has not been received from the one or more contacts after the predetermined period, the associated user manually initiates a telephone call to the one or more contacts with the portable communication device.

Another aspect of the invention relates to when the telephone call has not been received from the one or more contacts after the predetermined period, the portable communication device automatically initiates a telephone call to the one or more contacts.

One aspect of the present invention relates to a portable communication device including: radio circuitry coupled to a processor for receiving and/or transmitting a telephone call; a memory coupled to the processor, the memory including a queue indicative of a list of contacts that are required to contact an associated user of the portable communication device during a predetermined period; and upon receiving the telephone call, the processor compares a property of the incoming call with one or more properties associated with the queue to determine if the call is from one of the contacts provided in the queue; and the processor updates the list of contacts based upon the comparison made by the processor.

Another aspect of the invention relates to the portable communication device being a mobile telephone.

Another aspect of the invention relates to the queue including at least one authorized telephone number associated with each of the contacts.

Another aspect of the invention relates to the at least one property is the telephone number of the device that placed the incoming call.

Another aspect of the invention relates to if the associated user of the portable communication device is unavailable when the incoming call is received, the processor causes a prerecorded message stored in memory to be rendered to the contact.

Another aspect of the invention relates to including the processor updating the queue to indicate receipt of the incoming telephone call from the contact and the contact remains in the queue.

Another aspect of the invention relates to if the user of the portable communication device is available when the incoming telephone call is received, the processor facilitates communication between the contact and the associated user.

Another aspect of the invention relates to including the processor updating the queue to indicate receipt of the telephone call from one of the contacts listed in the queue.

Another aspect of the invention relates to the processor updating the queue by deleting the contact that initiated the telephone call from the queue.

Another aspect of the invention relates to a computer program stored on a machine readable medium, the program being suitable for use in an electronic equipment as an electronic appointment application including a queue indicative of a plurality of contacts that are required to contact an associated user of the portable communication device during a predetermined period from an authorized contact number, wherein: when the program is loaded in memory in the electronic equipment and executed causes the electronic equipment to process incoming telephone calls to determine if the telephone call is from one of the authorized contact numbers associated with one of the contacts from the queue; and updating the queue to indicate receipt of the telephone call from one of the contacts listed in the queue.

To the accomplishment of the foregoing and the related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be suitably employed.

Other systems, methods, features, and advantages of the invention will be or become apparent to one with skill in the art upon examination of the following drawings and detailed description. It is intended that all such additional systems, methods, features, and advantages be included within this description, be within the scope of the present invention, and be protected by the accompanying claims.

Although the invention is shown and described with respect to one or more embodiments, it is to be understood that equivalents and modifications will occur to others skilled in the art upon the reading and understanding of the specification. The present invention includes all such equivalents and modifications, and is limited only by the scope of the claims.

Also, although the various features are described and are illustrated in respective drawings/embodiments, it will be appreciated that features of the given drawing or embodiment may be used in one or more other drawings or embodiments of the invention.

It should be emphasized that the term "comprise/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Likewise, elements and features depicted in one drawing may be combined with elements and features depicted in additional drawings. Moreover, in the drawings, like reference numerals designate corresponding parts throughout the several views.

FIG. 1 is an exemplary schematic diagram illustrating an electronic equipment in accordance with aspects of the present invention.

FIG. 2 is a function block diagram of the electronic equipment of FIG. 1 in accordance with aspects of the present invention.

FIG. 3 is an exemplary queue illustrating a exemplary portion of the appointment application program in accordance with aspects of the present invention.

DETAILED DESCRIPTION OF EMBODIMENTS

Figure 4:
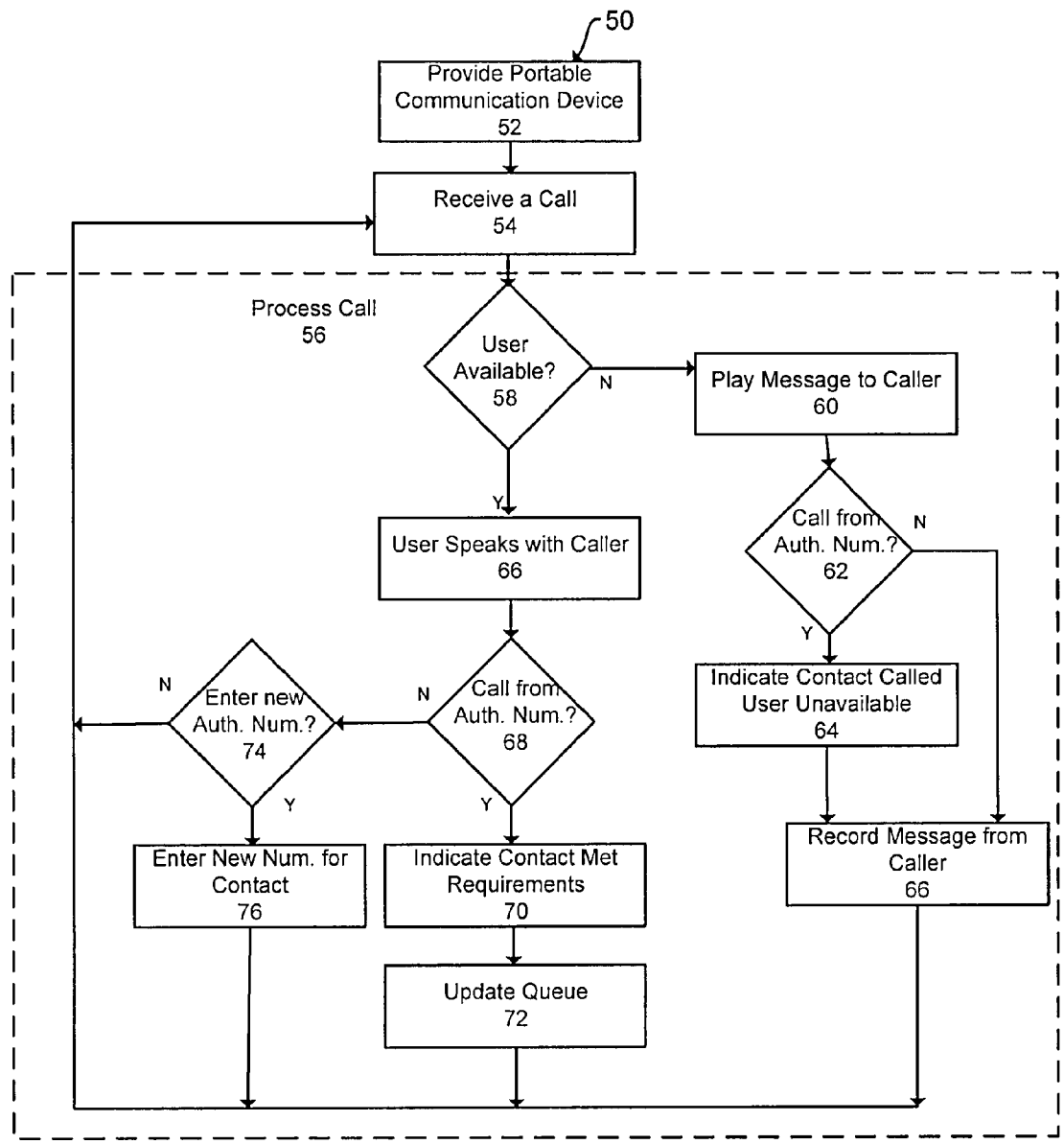
FIGS. 4 and 5 are exemplary methods in accordance with aspects of the present invention.

The present invention will now be described with reference to the drawings, wherein like reference numerals are used to refer to like elements throughout.

The term "portable communication device" includes any portable electronic equipment including, for example, mobile radio terminals, mobile telephones, mobile devices, mobile terminals, communicators, pagers, electronic organizers, personal digital assistants, smartphones and the like. The term "portable communication device" also may include portable digital music players and/or video display devices, e.g., iPod devices, MP3 players, DVD players, etc.

In the present application, aspects of the invention are described primarily in the context of a mobile telephone. However, it will be appreciated that the invention is not intended to be limited to a mobile telephone and can be any type of electronic equipment. In general, aspects of the present invention relate to a portable communication device, method and computer program for keeping track of communications with a predetermined group of individuals (e.g., clients, patients, customers, other individuals, etc.), generally referred to hereinafter as "contacts".

Referring to FIG. 1, a portable communication device 10 in accordance with aspects of the present invention is illustrated. The portable communication device 10 may include a user interface 12 that enables the user easily and efficiently to perform one or more communication tasks (e.g., identify a contact, select a contact, make a telephone call, receive a telephone call, look up a telephone number, maintain various appointment logs, etc). The user interface 12 of the portable communication device 10 generally includes one or more of the following components: a display 14, an alphanumeric keypad 16, function keys 18, a speaker 20, and a microphone 22.

As shown in FIG. 2, the portable communication device 10 further includes one or more storage devices 24 (e.g., memory, RAM, ROM, etc.) capable of storing application software, including an electronic appointment application 26. The appointment application 26 is generally coupled to a processor 28. The processor 28 is programmed to perform the functionality described herein, including coordinating a communication session between an individual and a user of the portable communication device 10, maintaining and updating a queue of contacts that is required to contact the user of the portable communication device 10 during a predetermined time period.

The processor 28 also is coupled with conventional input devices (e.g., alphanumeric keypad 16, function keys 18, microphone 22, etc.), and to the device display 20. The user interface 12 facilitates controlling operation of the portable communication device 10 including initiating and conducting telephone calls and other communications. The user interface 12 is also one mechanism for the user or operator of the portable communication device 10 to manipulate the electronic phonebook application 26.

An electronic appointment application 26 may take a variety of forms. For example as shown in FIG. 3, the electronic appointment application 26 may include a plurality of contacts in the form of a queue 30. The plurality of contacts in the queue 30 may be structured in any desired manner. In one exemplary embodiment, the queue 30 may include one or more of the following fields: Queue Order, Name, one or more contact Telephone Numbers, Frequency (Freq.), Met. Requirements (Met. Req.), received call unavailable to speak with caller (RCU).

The Queue Order field may be the order that the contact is organized in the queue 30. The Queue Order field may be set an in any desired manner. For example, it may desirable to order (or prioritize) certain contacts above other contacts (e.g., individuals having serious illnesses over individuals having less serious illnesses, individuals having a propensity for violence over non-violent individuals, etc.). The Queue Order may be fixed and/or modified at any desired time.

In one embodiment, the appointment application 26 is configured to communicate with a personal computer and/or contact applications running on the personal computer to add, modify, delete or otherwise edit information pertaining to one or more contacts stored in either the portable communication device 10 or the personal computer (e.g., synchronize modification made on the portable communication device 10 to the personal computer and vice versa).

The Name field is generally the identity of the contact that is being monitored. In general, the contact is required to call the person with the portable communication device 10 at a predetermined frequency, as discussed below. As shown, each individual may provide multiple telephone numbers and/or other authorized contact numbers. As shown in FIG. 3, the contacts may provide up to three authorized contact numbers (e.g., telephone numbers). These telephone numbers are referred to interchangeably herein as authorized telephone numbers, since they may be programmed in the application and allows the processor to determine if a received call is from one of the contacts. One of ordinary skill in the art will readily appreciate that other identification means may be available, for example identification numbers associated with the telephone that contact is using to call, etc.

If the calling individual was permitted to call from any telephone, it would be more difficult for the user of the portable communication device 10 to determine if a call was received from an unauthorized number. For example, after receiving the call, the call receiver would be required to add a contact number for the individual or otherwise keep track of the calling information on a separate sheet of paper.

The Frequency field refers to how frequently the caller is required to call the owner of the portable communication device 10. Any frequency may be used in accordance with aspects of the present invention. For example, the contact may be required to call daily, weekly, monthly, etc.

The Met Requirements field refers to the user contacting the user of the portable communication device 10 and meeting the prescribed requirements. Such requirements may be speaking with the user of the device 10 and/or leaving a message for the user. As discussed herein, the Met Requirements field is satisfied when the user receives a call from the individual contact from an authorized number and speaks to the contact during the specified time frame. In this example, these acts would fulfill the individual's calling requirements and result in "Y" in Met Requirements field.

The Received Communication Unavailable (RCU) field refers to the situation when the caller calls, as required, but the individual receiving the call is unable to speak with the caller. For example, if the individual receiving the call is a psychiatrist, the psychiatrist may be meeting with another patient and is unavailable to take any calls from other patients. In such a situation, the caller may leave a message for the user to get back him, as described below.

One of ordinary skill will readily appreciate that the fields disclosed above are exemplary and more or fewer fields may be provided depending on the precise application. Such fields may include, for example, e-mail addresses, home address, pictures, etc.)

FIG. 3 illustrates an embodiment of the present invention, wherein the queue order is based on the frequency in which the caller must call. For example, Jane Doe and Alan are required to call daily; Zack is required to call weekly; Mo Rice and Paige are required to call monthly. One of ordinary skill will readily appreciate that separate queues may be used for callers having different calling frequencies and/or different medical, support, psychological, legal and/or any other issues.

One aspect of the present invention is to allow the user manually to enter a value for a particular contact or group of contacts. For example, when a user calls from an authorized telephone number and speaks with the individual receiving the call, the call receiver may manually set the "Met Requirements" field to "Yes" to remove the individual from the queue for the specified period.

FIG. 4 illustrates an exemplary method 50 for coordinating a communication session between an individual and a user of a portable communication device. At block 52, a portable communication device 10 is provided. The portable communication device 10 includes an appointment application program 26 stored in memory 24. The program 26 includes a queue 30 indicative of a plurality of contacts that are required to contact an associated user of the portable communication device during a predetermined period from an authorized contact number.

At block 54, a telephone call is received by the portable communication device 10. At block 56, the processor processes the telephone call as described below. For example, the processor 28 processes the telephone call to determine if the telephone call is from one of the authorized contact numbers (e.g., authorized telephone numbers) associated with one of the contacts from queue.

Upon receiving a call (from block 54), at block 58, a determination is made as to if the user of the portable communication device 10 is available to speak with the caller. As one of ordinary skill will readily appreciate, this may done in number of ways. For example, the user may set a profile to meeting and/or do not disturb mode, in which case the processor would determine that the user is unavailable. If the user is unavailable, at block 60, a message is rendered to the caller. At block 62, the processor determines if the call was from an authorized telephone number of one of the contacts. At block 64, if the call was from an authorized telephone number, a designation may be made in the application program (e.g., a "Y" may be entered in the Received Call Unavailable (RCU) field (FIG. 3)). At block 66, the caller may have the option to leave a message for the user of the portable communication device 10.

At block 66, if the user of the portable communication device 10 is available to speak with the caller, the caller may speak with the user. At block 68, the processor determines if the call is from an authorized telephone number associated with one of the contacts. If the call is from an authorized number, at block 70, the processor updates one or more fields of the computer program 26 to indicate that the caller met his or her periodic requirements. At block 72, the queue 30 is updated to indicate that the contact met his or her periodic calling requirements.

If at block 68, the processor determines that the call is from an unauthorized telephone number, the user of the portable communication device 10 may provided be an opportunity to assign the telephone number to the contact, at block 74. If the user chooses to enter a new authorized number for the contact, data flow is directed to block 76. At block 76, the user may enter the new authorized number. One of ordinary skill in the art will readily appreciate that there are a number of ways to enter the new authorized number (e.g., by automatically inserting the number, manually entering the number, cut and pasting the number, etc.). Once the new number has been entered in to the application program 26, the next time the contact calls from the newly authorized number, the processor will process the call automatically, without requiring additional user input.

If all of the contacts that are required to call a user during a predefined period actually call and meet their requirements, the application may reset for the next time period of interest. On the other hand, if one or more of the contacts have not and/or did not call during the predefined period or as desired by the user of the portable communication device 10, the user may initiate a telephone call to the one or more contacts. The call or calls may be generated manually and/or automatically.

Figure 5:
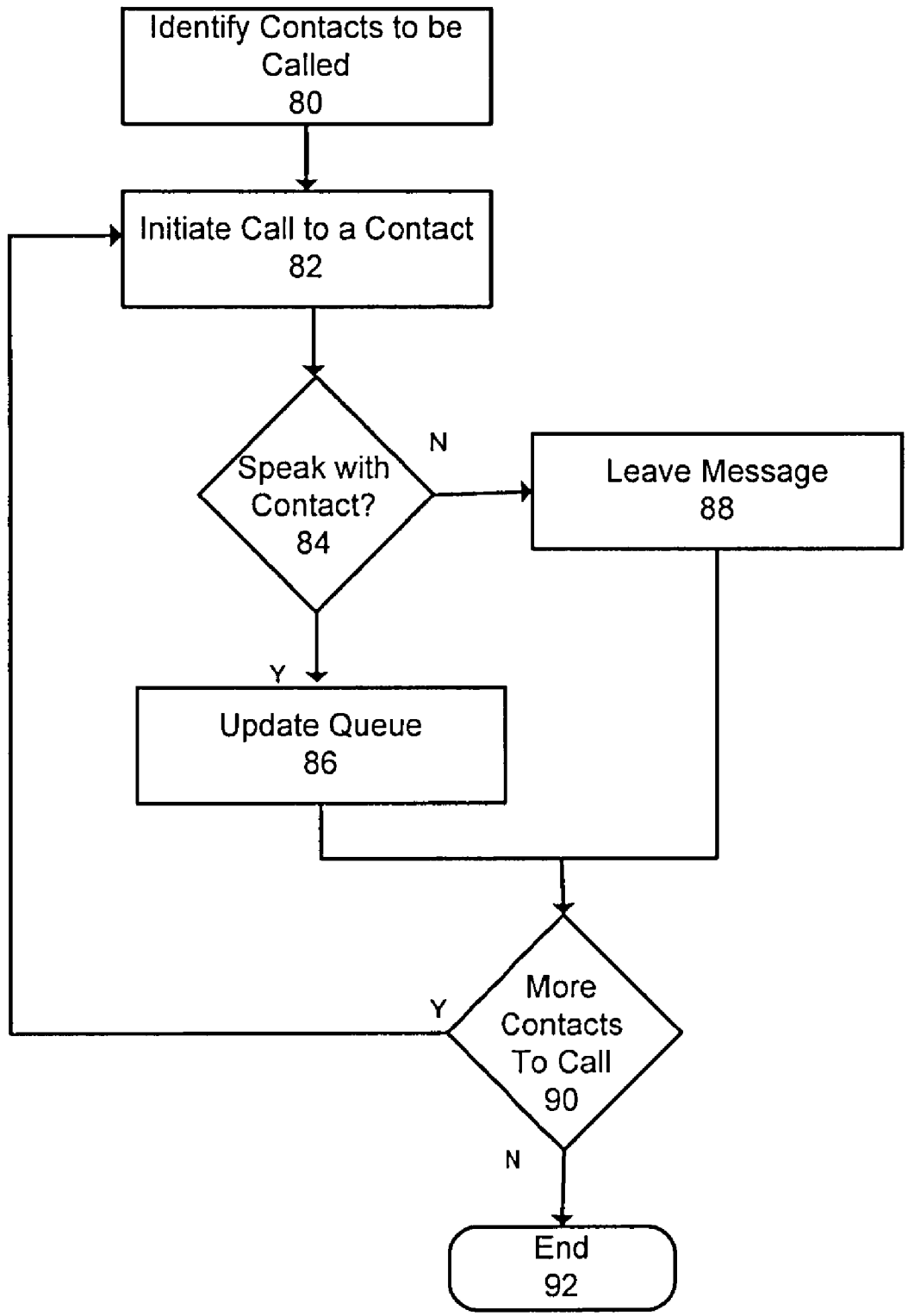

Referring to FIG. 5, at the end of the predefined period, an exemplary method is identified for initiating a communication session with one or more contacts. At block 80, contacts that did not fulfill their calling requirements are identified. This may be accomplished by reviewing one or more fields in the computer application 26 and/or fields in the queue 30. Once one or contacts are identified, a call is initiated from portable communication device 10 to the contact, at block 82. The call may be manually dialed or the computer application 26 may include an auto-dial function 32 (shown in FIG. 2) that selects a contact and automatically dials one or more contacts associated with the contact, based on any selected user criteria.

At block 84, a determination is made as to whether the user actually spoke with the contact. This determination may be made by the user manually using an input device and/or processing the incoming sound to determine if a live voice or a prerecorded voice is detected. If the user of the portable communication device 10 spoke with the contact, at block 86 the queue 30 is updated to indicate that the contact met their requirements and the contact may be removed from the queue. If the user does not speak with the contact, at block 88 the user may optionally leave a message for the contact.

From blocks 86 and 88, data flows to block 90, where a determination is made if there are any additional contacts to call. One of ordinary skill in the art will readily appreciate that this may be done in a variety of ways. For example, searching the Met Requirements field of the Queue or having an empty queue depending on how the queue 30 is updated.

If there are additional contacts to call, data flow returns to block 82 and repeats as described above until no contacts are available and/or may be ceased by the user. If there are no additional contacts to call, the process terminates at block 92.

There are a variety of enhancements to the above described methods. For example, if a contact fails to call the user a predetermined number of times, there can be consequences for the contact. Such consequences may include increase cost of the service, since the burden falls on the user of the portable communication device to call the contact. Another consequence may be to remove the contact from the queue and require the contact to physically visit the user of the portable communication device and/or a colleague or other third party to meet their requirements.

The appointment application is preferably compatible with other contact, calendar applications such as, for example, Microsoft Outlook, GroupWise, ACT, etc. The user may interact with one or more of these applications and synchronize or otherwise transfer the data from a personal computer to the portable communication device 10.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for coordinating a communication session between an individual and a user of a portable communication device, the method comprising:

receiving a telephone call from the individual at a portable communication device, wherein the portable communication device includes a processor; and an appointment application stored in a memory of the portable communication device, wherein the processor is coupled to the memory and the appointment application includes a queue indicative of a plurality of contacts that are required to contact an associated user of the portable communication device during a predetermined period from an authorized contact number;

processing the telephone call by the processor to determine if the telephone call is from one of the authorized contact numbers associated with one of the contacts from queue; and updating the queue by the processor to indicate receipt of the telephone call from one of the contacts listed in the queue.

2. The method of claim 1, wherein the portable communication device is a mobile telephone.

3. The method of claim 1, wherein the authorized contact number is a telephone number.

4. The method of claim 1, wherein if the user of the portable communication device is unavailable when the telephone call is received, a prerecorded message is rendered to the calling contact.

5. The method of claim 4 the step of updating the queue to indicate receipt of the telephone call from the contact includes maintaining the contact in the queue.

6. The method of claim 1, wherein if the user of the portable communication device is available when the contact calls, the contact and the associated user converse as desired.

7. The method of claim 1, wherein the queue is updated by deleting the contact that initiated the telephone call from the queue.

8. The method of claim 1, wherein when the telephone call has not been received from the one or more contacts after the predetermined period, the associated user manually initiates a telephone call to the one or more contacts with the portable communication device.

9. The method of claim 1, wherein when the telephone call has not been received from the one or more contacts after the predetermined period, the portable communication device automatically initiates a telephone call to the one or more contacts.

10. A portable communication device comprising:
radio circuitry coupled to a processor for receiving and/or transmitting a telephone call;
a memory coupled to the processor, the memory including an appointment application that includes a queue indicative of a list of contacts that are required to contact an associated user of the portable communication device during a predetermined period and an authorized contact number for each contact; and upon receiving the telephone call, the processor processes the telephone call to determine if the telephone call is from the authorized contact number associated with one of the contacts; and the processor updates the queue to indicate receipt of the telephone call from one of the contacts listed in the queue.

11. The device of claim 10, wherein the portable communication device is a mobile telephone.

12. The device of claim 10, wherein the queue includes at least one authorized telephone number associated with each of the contacts.

13. The device of claim 10, wherein if the associated user of the portable communication device is unavailable when the incoming call is received, the processor causes a prerecorded message stored in memory to be rendered to the contact.

14. The device of claim 13 further including the processor updates the queue to indicate receipt of the incoming telephone call from the contact and the contact remains in the queue.

15. The device of claim 10, wherein if the user of the portable communication device is available when the incoming telephone call is received, the processor facilitates communication between the contact and the associated user.

16. The device of claim 15, wherein the processor updates the queue by deleting the contact that initiated the telephone call from the queue.

* * * * *